United States Patent [19]
Nickl et al.

[11] 3,939,268
[45] Feb. 17, 1976

[54] 2,4-DIAMINO SUBSTITUTED PYRIDOL(3,2-D)PYRIMIDINE AS ANTITHROMBOTIC AGENTS

[75] Inventors: Josef Nickl; Erich Muller; Berthold Narr; Josef Roch, all of Biberach, Riss, Germany

[73] Assignee: Boehringer Ingelheim GmbH, Ingelheim am Rhein, Germany

[22] Filed: Sept. 4, 1974

[21] Appl. No.: 503,073

Related U.S. Application Data

[62] Division of Ser. No. 241,791, April 6, 1972, Pat. No. 3,843,638.

[30] Foreign Application Priority Data

Apr. 10, 1971 Germany............................ 2117657
Feb. 23, 1972 Germany............................ 2208534
Feb. 23, 1972 Germany............................ 2208535

[52] U.S. Cl. ................. 424/246; 424/248; 424/250
[51] Int. Cl.²................A61K 31/54; A61K 31/495; A61K 31/535
[58] Field of Search .......... 424/200, 246, 248, 251, 424/253, 250

[56] References Cited
UNITED STATES PATENTS

| | | | |
|---|---|---|---|
| 2,937,284 | 5/1960 | Hitchings et al. ............. | 260/256.4 F |
| 3,248,395 | 4/1966 | Ohnacker..................... | 260/256.4 F |
| 3,534,039 | 10/1970 | Davoll ......................... | 260/256.4 F |

Primary Examiner—Stanley J. Friedman
Attorney, Agent, or Firm—Hammond & Littell

[57] ABSTRACT

Pharmaceutical compositions containing as an active ingredient a compound of the formula

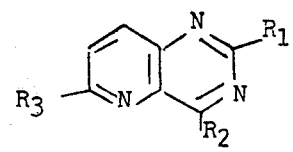

wherein
$R_1$ and $R_2$, which may be identical to or different from each other, are each morpholino, thiomorpholino, 1-oxido-thiomorpholino, 1,1-dioxidothiomorpholino or piperidino, where each of these may optionally have a lower alkyl substituent attached thereto; piperazino; N'-acyl-piperazino; N'-carbamoyl-piperazino; N'-lower alkyl-piperazino; dialkanol-amino; or alkylenediamino; and
$R_3$ is hydrogen or methyl;
or a non-toxic, pharmacologically acceptable acid addition salt thereof; and methods of using the same to inhibit thrombocyte aggregation and adhesiveness.

9 Claims, No Drawings

2,4-DIAMINO SUBSTITUTED PYRIDOL(3,2-D)PYRIMIDINE AS ANTITHROMBOTIC AGENTS

This is a division of copending application Ser. No. 241,791 filed Apr. 6, 1972, now U.S. Pat. No. 3,843,638.

This invention relates to novel pharmaceutical compositions containing a 2,4-diamino-substituted pyrido[3,2-d]pyrimidine or a non-toxic acid addition salt thereof, as well as to methods of inhibiting thrombocyte aggregation and adhesiveness therewith.

More particularly, the present invention relates to pharmaceutical compositions containing as an active ingredient a compound of the formula

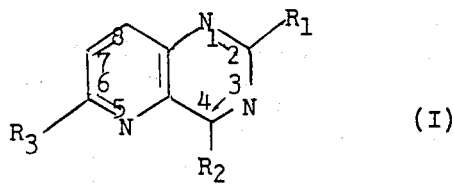

wherein $R_1$ and $R_2$, which may be identical to or different from each other, are each morpholino, thiomorpholino, 1-oxido-thiomorpholino, 1,1-dioxidothiomorpholino or piperidono, where each of these may optionally have a lower alkyl substituent attached thereto; piperazino; N'-acyl-piperazino; N'-carbamoyl-piperazino; N'-lower alkyl-piperazino; dialkanol-amino; or alkylenediamino; and $R_3$ is hydrogen or methyl;

or a non-toxic, pharmacologically acceptable acid addition salt thereof.

The compounds embraced by formula I may be prepared by the following methods:

Method A

By reacting a di- or tri-substituted pyrido[3,2-d]pyrimidine of the formula

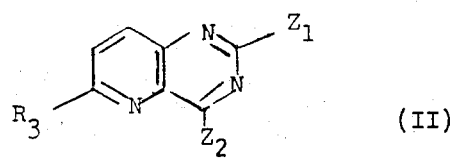

wherein one of $Z_1$ and $Z_2$ is a substituent exchangeable for an amino-substituent included in the definition of $R_1$ and $R_2$ in connection with formula I, such as halogen or an alkyl-, aryl- or aralkyl-substituted hydroxy, mercapto, sulfinyl or sulfonyl group, the other of $Z_1$ and $Z_2$ has a meaning defined for $R_1$ and $R_2$ in formula I, and $R_3$ has the meanings defined in formula I, with an amine of the formula

respectively, where $R_1$ and $R_2$ have the same meanings as in formula I.

The substituent exchange reaction is carried out, depending upon the reactivity of the exchangeable substituent $Z_1$ or $Z_2$, at a temperature between 0° and +250°C, optionally in the presence of an acid-binding agent, and advantageously in a solvent medium, such as dioxane, glycol dimethyl ether or an excess of the amine reactant of the formula III.

In those instances where $Z_1$ is halogen or an alkyl-, aryl- or aralkyl-substituted sulfinyl or sulfonyl group, the reaction is preferably performed at a temperature between 80° and 110°C; on the other hand, if $Z_1$ is an alkyl-, aryl- or aralkyl-substituted hydroxyl or mercapto group, the reaction is carried out within a preferred temperature range of 150° to 200°C, if necessary in a pressure vessel.

In those instances where $Z_2$ is halogen or an alkyl-, aryl- or aralkyl-substituted sulfinyl or sulfonyl group, the reaction is preferably performed at a temperature between 0° and +40°C; on the other hand, if $Z_2$ is an alkyl-, aryl- or aralkyl-substituted hydroxyl or mercapto group, the preferred reaction temperature is between 80° and 150°C.

If it is desired to prepare a compound of the formula I wherein $R_1$ and $R_2$ are identical to each other, the starting compound of the formula II may also be one wherein $Z_1$ and $Z_2$ are both exchangeable substituents, as defined in connection with formula II; in that case the substituent exchange reaction proceeds stepwise. For instance, if the starting compound of the formula II is 2,4-dichloro-6-methyl-pyrido[3,2-d]pyrimidine, the chlorine atom in the 4-position is exchanged for the amino-substituent at temperatures as low as 0° to +40°C, while the chlorine atom in the 2-position is not exchanged until more elevated reaction temperatures are applied.

Method B

For the preparation of a compound of the formula I wherein one of $R_1$ and $R_2$ is unsubstituted piperazino and the other has the meanings defined for $R_1$ and $R_2$ in connection with formula I except N'-acyl-piperazino, by deacylating a di- or tri-substituted pyrido[3,2-d]pyrimidine of the formula

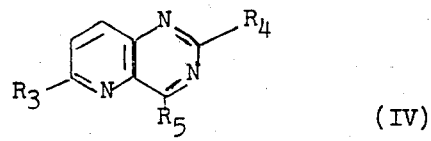

wherein $R_3$ has the same meanings as in formula I, one of substituents $R_4$ and $R_5$ is N'-acyl-piperazino and the other has a meaning defined for $R_1$ and $R_2$ in connection with formula I.

The de-acylation is preferably carried out by hydrolysis in the presence of an inorganic base, such as potassium hydroxide, or of an acid, such as hydrochloride acid, advantageously in a solvent medium, such as water or isopropanol, and at a temperature up to the boiling point of the particular solvent medium.

In those instances where method A or B yields a compound of the formula I wherein $R_1$ and/or $R_2$ are unsubstituted piperazino, these may, if desired, subsequently be acylated by conventional methods. The acylation is preferably effected with a corresponding acid halide or acid anhydride, or with the corresponding acid in the presence of a dehydrating agent, such as N,N'-dicyclohexylcarbodiimide, or in an apparatus provided with a water separator; a carbamoyl substituent is advantageously introduced by reaction with an alkali metal cyanate in weakly acid solution.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, lactic acid, citric acid, tartaric acid, maleic acid, 8-chlorotheophylline or the like.

The starting compounds needed for methods A and B are either known compounds or may be prepared by methods described in the literature.

For instance, a corresponding 2-chloro-4-amino-substituted pyrido[3,2-d]pyrimidine of the formula II may be obtained by reacting 2,4-dichloro-pyrido[3,2-d]pyrimidine [see J.A.C.S. 78, 973 (1956); J. Chem. Soc. 1956, 1045; and J. Chem. Soc. 1956, 4433] with a corresponding amine at relatively low temperatures, such as 0° to 40°C [see also W. J. Irwin et al., Advances in Heterocyclic Chemistry 10, 149 (1969)].

Mild hydrolysis of 2,4-dichloro-pyrido[3,2d]pyrimidine with one equivalent of an alkali metal hydroxide at relatively low temperatures yields 2-chloro-4-hydroxypyrido [3,2-d]pyrimidine, which is subsequently reacted with a corresponding amine at more elevated temperatures to yield a corresponding 2-amino-4-hydroxy-substituted pyrido [3,2-d]pyrimidine which, in turn, is subsequently converted into the corresponding 2-amino-4-halo-substituted pyrido [3,2-d]pyrimidine of the formula II by conventional methods.

A halo-substituted pyrido[3,2-d]pyrimidine of the formula II may be converted into a correspondingly substituted mercapto- or hydroxy-pyrido[3,2-d]pyrimidine of the formula II by reaction with a corresponding mercaptor hydroxy-compound in the presence of a strong base. A mercapto-substituted pyrido[3,2-d]pyrimidine of the formula II thus obtained may, in turn, be converted into a corresponding sulfinyl- or sulfonyl-substituted pyrido[3,2-d] pyrimidine of the formula II by oxidation.

A starting compound of the formula IV may be obtained by method A above.

The following examples illustrate the preparation of a starting compound of the formula IV as well as of end products of the formula I.

Preparation of a starting compound of the formula IV

EXAMPLE A

2-Piperazino-4-ethylmercapto-pyrido[3,2-d]pyrimidine a. 2-Chloro-4-ethylmercapto-pyrido[3,2]pyrimidine A suspension of 15 gm (0.075 mol) of 2,4-dichloropyrido[3,2-d]pyrimidine in 100 ml of acetone at −40°C was admixed with a solution of 3.2 gm (0.08 mol) of sodium hydroxide and 4.9 gm (5.8 ml) of ethylmercaptan in 25 ml of water, and the mixture was stirred for two hours at room temperature. Thereafter, 200 ml of water were added to the reaction mixture, and the precipitate formed thereby was collected and recrystallized from petroleum ether, yielding 11.0 gm (65% of theory) of 2-chloro-4-ethylmercapto-pyrido[3,2-d]pyrimidine, m.p. 101°–103°C.

b. 2-Piperazino-4-ethylmercapto-pyrido[3,2-d]pyrimidine

A mixture consisting of 5 gm (0.022 mol) of the end product obtained in (a), 4.7 gm (0.055 mol) of anhydrous piperazine and 20 ml of dioxane was heated at its boiling point for 15 minutes. Thereafter, the resulting solution was evaporated, the residue was taken up in 2N acetic acid, and the solution was filtered. The filtrate was made alkaline with 4N sodium hydroxide, and the precipitate formed thereby was collected and recrystallized from benzene/cyclo-hexane, yielding 3.6 gm (59% of theory) of 2-piperazino-4-ethylmercapto-pyrido[3,2-d]pyrimidine, m.p. 98°–101°C.

Preparation of end products of the formula I.

EXAMPLE 1

2-Piperazino-4-thiomorpholino-pyrido[3,2-d]pyrimidine by method A 18.0 gm (0.0715 mol) of 2-chloro-4-thiomorpholino-pyrido[3,2-d]pyrimidine (m.p. 162°–164°C), encased in a liquid-permeable envelope, were extracted therefrom by placing it into a boiling solution of 30.6 gm (0.356 mol) of anhydrous piperazine in 150 ml of dioxane; the extraction was completed after about 5 hours. Thereafter, the reaction solution was evaporated, the residue was taken up in a mixture of water and benzene, and the organic phase was separated and evaporated. The residue was dissolved in 300 ml of methanol, the resulting solution was filtered, the filtrate was again evaporated, and the residue was recrystallized from 600 ml of cyclohexane. Upon working up the mother liquors, a total of 17.3 gm (76.5% of theory) of the compound of the formula

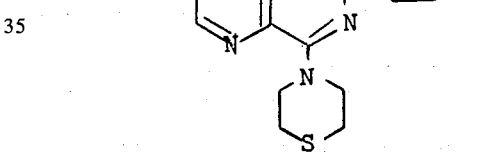

having a melting point of 144°–145°C, was obtained.

Its hydrochloride hydrate had a melting point of 220°–225°C (decomp.; recrystallized from ethanol);

Its dihydrobromide hydrate had a melting point of 114°–115°C (decomp.);

Its maleate had a melting point of 190°–191°C (recrystallized from methanol).

The same compound was obtained from the same reactants by boiling for one hour in 1,2-dimethoxyethane; yielding 72of theory, m.p. 143°–144°C.

EXAMPLE 2

Using a proceedure analogous to that described in Example 1, 2-(N'-carbethoxy-piperazino)-4-thiomorpholino-pyrido[3,2-d]pyrimidine, m.p. 153°–154°C (recrystallized from ethanol, of the formula

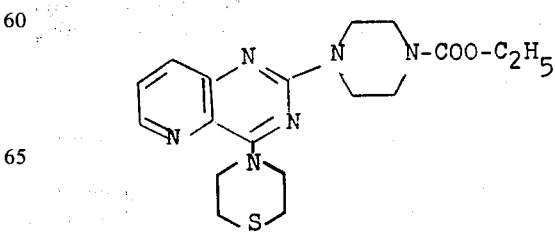

was prepared from 2-chloro-4-thiomorpholino-pyrido[3,2-d] pyrimidine and N-carbethoxy-piperazine. The yield was 83% of theory.

EXAMPLE 3

Using a proceedure analogous to that described in Example 1, 2-(N'-benzoyl-piperazino)-4-thiomorpholinopyrido [3,2-d]pyrimidine, m.p. 168°–170°C (recrystallized from isopropanol) of the formula

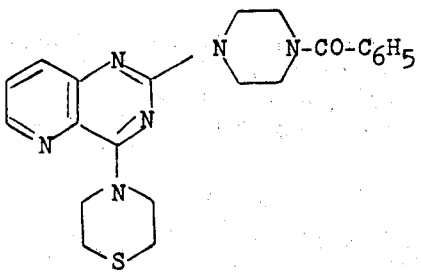

was prepared from 2-chloro-4-thiomorpholino-pyrido[3,2-d] pyrimidine and N-benzyol-piperazine. The yield was 85% of theory.

EXAMPLE 4

Using a procedure analogous to that described in Example 1, 2-[N'-(p-toluene-sulfonyl)-piperazino]-4-thiomorpholino-pyrido[3,2-d]pyrimidine, m.p. 195°–196°C (recrystallized from benzene/petroleum ether), of the formula

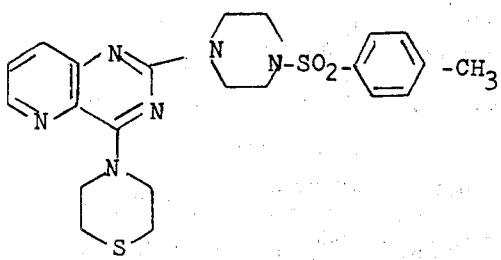

was prepared from 2-chloro-4-thiomorpholino-pyrido[3,2-d] pyrimidine and N-(p-toluene-sulfonyl)-piperazine. The yield was 76% of theory.

EXAMPLE 5

Using a procedure analogous to that described in Example 1, 2-(N'-methyl-piperazino)-4-thiomorpholinopyrido [3,2-d]pyrimidine, m.p. 133°–135°C (recrystallized from ethyl acetate), of the formual

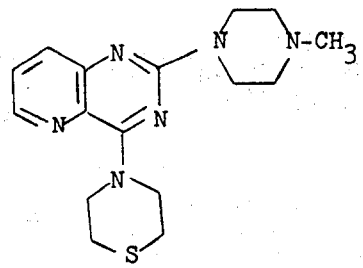

was prepared from 2-chloro-4-thiomorpholino-pyrido[3,2-d] pyrimidine and N-methyl-piperazine. The yield was 69% of theory. Its dihydrochloride had a melting point of 272°–274°C (decomp.).

EXAMPLE 6

Using a procedure analogous to that described in Example 1, 2-(di-propanol-amino)-4-thiomorpholino-pyrido [3,2-d]]pyrimidine, m.p. 115°–116°C (recrystallized from ethyl acetate), of the formula

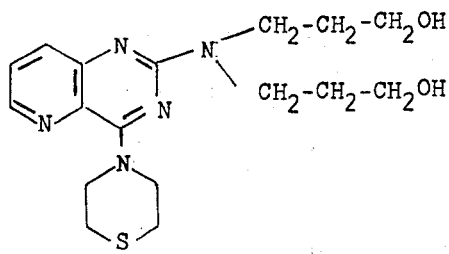

was prepared from 2-chloro-4-thiomorpholino-pyrido[3,2-d] pyrimidine and dipropanol-amine. The yield was 50% of theory. Its hydrochloride had a melting point of 186°–188°C (recrystallized from n-propanol).

EXAMPLE 7

Using a procedure analogous to that described in Example 1, 2-(diethanol-amino)-4-thiomorpholino-pyrido[3,2-d]pyrimidine, m.p. 114°–115°C (recrystallized from ethyl acetate), of the formula

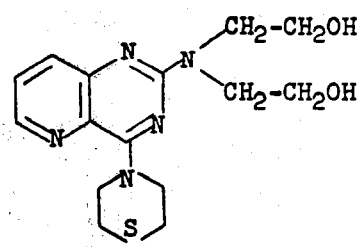

was prepared from 2-chloro-4-thiomorpholino-pyrido[3,2-d] pyrimidine and diethanol-amine. The yield was 72% of theory. Its hydrochloride had a melting point of 212°–213°C (decomp.; recrystallized from methanol).

EXAMPLE 8

2-Piperazino-4-(1'-oxido-thiomorpholino)-pyrido[3,2-d]pyrimidine by method A 24.0 gm (0.085 mol) of 2-chloro-4-(1'-oxido-thiomorpholino)-pyrido[3,2-d]pyrimidine (m.p. 198°–200°C, decomp.) were added gradually over a period of one hour to a boiling solution of 36.6 gm (0.425 mol) of anhydrous piperazine in 240 ml of dioxane (or 1,2-dimethoxy-ethane), and the resulting mixture was refluxed for 2½ hours. Thereafter, the reaction solution was evaporated, the residue was dissolved in 180 ml of hot water, and the small amount of insoluble material was filtered off. The filtrate was extracted eight times with 50 ml each of a mixture of chloroform and methanol (4:1), and each extract was washed twice with 50 ml of water each. The organic phases thus freed from excess piperzaine were combined, dried and evaporated. The residue was digested with benzene, collected by vacuum filtration and then recrystallized from ethyl acetate, yielding 23.8 gm (84% of theory) of the compound of the formula

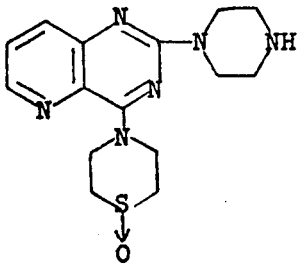

having a melting point of 200°–202°C. Its dihydrochloride had a melting point of 305°–307°C (decomp.; recrystallized from 80% ethanol).

EXAMPLE 9

Using a procedure analogous to that described in Example 1, 2-(N'-methyl-piperazino)-4-(1'-oxido-thiomorpholino)-[3,2-d]pyrimidine, m.p. 192°–194°C (recrystallized from benzene), was prepared from 2-chloro-4-(1'-oxido-thiomorpholino)-pyrido[3,2-d]pyrimidine, m.p. 198°–200°C (decomp.), and N-methyl-piperazine. It dihydrochloride had a melting point of 260°–261°C (decomp., recrystallized from ethanol). The yield was 82% of theory.

EXAMPLE 10

Using a procedure analogous to that described in Example 1, 2-(dipropanol-amino)-4-(1'-oxido-thiomorpholinopyrido[3,2-d]pyrimidine, m.p. 146°–148°C (recrystallized from benzene), was prepared from 2-chloro-4-(1'-oxido-thiomorpholino)-pyrido[3,2-d]pyrimidine and dipropanol-amine. Its hydrochloride had a melting point of 202°–203°C (recrystallized from ethanol/ether). The yield was 73% of theory.

EXAMPLE 11

Using a procedure analogous to that described in Example 1, 2-(N-ethanol-hexanolamino)-4-(1'-oxido-thiomorpholino-pyrido[3,2-d]pyrimidine was prepared from 2-chloro-4-(1'-oxido-thiomorpholino)-pyrido[3,2-d]pyrimidine and N-ethanol-hexanolamine. Its hydrochloride had a melting point of 192°–193°C (recrystallized from ethanol/ether). The yield was 71% of theory.

EXAMPLE 12

Using a procedure analogous to that described in Example 1, 2-morpholino-4-(1'-oxido-thiomorpholinopyrido [3,2-d]pyrimidine, m.p. 218°–220°C, of the formula

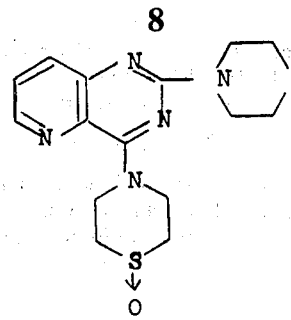

was prepared from 2-chloro-4-(1'-oxido-thiomorpholino)-pyrido[3,2-d]pyrimidine and morpholine. Its hydrochloride had a melting point of 262°–263°C (decomp.; recrystallized from ethanol). The yield was 83% of theory.

EXAMPLE 13

Using a proceedure analogous to that described in Example 8, 2-ethylenediamino-4-(1'-oxido-thiomorpholinopyrido[3,2-d]pyrimidine of the formula

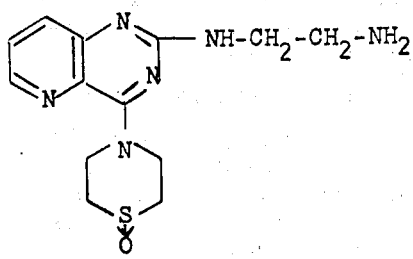

was prepared from 2-chloro-4-(1'-oxido-thiomorpholino)-pyrido [3,2-d]pyrimidine and ethylenediamine. Its dihydrochloride had a melting point of 299°–300°C (decomp.; recrystallized from methanol/water = 9:12). The yield was 17.5% of theory).

EXAMPLE 14

Using a procedure analogous to that described in Example 8, 2-piperazino-4-(1'-oxido-2'-methyl-thiomorpholino-pyrido[3,2-d]pyrimidine, m.p. 165°–167°C (recrystallized from benzene/cyclohexane), of the formula

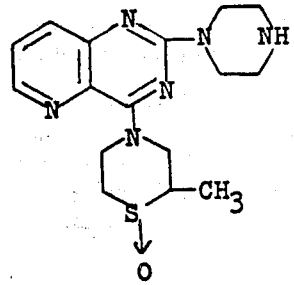

was prepared from 2-chloro-4-(1'-oxido-2'-methyl-thiomorpholino)-pyrido[3,2-d]pyrimidine, m.p. 196°–199°C and piperazine. The yield was 48% of theory.

EXAMPLE 15

Using a procedure analogous to that described in Example 1, 2-piperazino-4-morpholino-pyrido[3,2-d]pyrimidine, m.p. 167°–168°C (recrystallized from benzene), of the formula

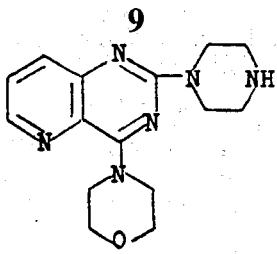

was prepared from 2-chloro-4-morpholino-pyrido[3,2-d]pyrimidine, m.p. 174°–175°C, and piperazine hexahydrate in glycol dimethylether. Its dihydrochloride hydrate had a melting point of 281°–283°C (recrystallized from ethanol). The yield was 74% of theory.

EXAMPLE 16

2-(N'-Methyl-piperazino)-4-morpholino-pyrido[3,2-d]pyrimidine by method A

A mixture consisting of 4.5 gm of 2-chloro-4-morpholino-pyrido[3,2-d]pyrimidine (m.p. 174°–175°C) and 15 ml of N-methyl-piperazine was heated at 110°C for 3½ hours. Thereafter, the reaction solution was cooled, then diluted with water, and the precipitate formed thereby was collected by vacuum filtration, dried and extracted with 200 ml of boiling cyclohexane. The extract was filtered, and the filtrate was evaporated, yielding 3.7 gm (66% of theory) of the compound of the formula

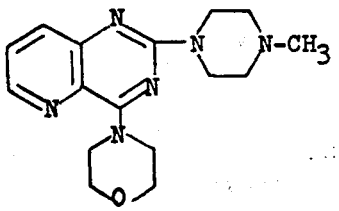

having a melting point of 142°–143°C. Its dihydrochloride had a melting point of 264°–267°C (recrystallized from ethanol).

EXAMPLE 17

Using a procedure analogous to that described in Example 16, 2-(diethanol-amino)-4-morpholino-pyrido[3,2-d]pyrimidine, m.p. 143°–145°C (recrystallized from benzene or ethyl acetate), was prepared from 2-chloro-4-morpholinopyrido[3,2-d]pyrimidine and diethanolamine. The yield was 38.6% of theory.

EXAMPLE 18

Using a procedure analogous to that described in Example 1, 2-(dipropanol-amino)-4-morpholino-pyrido[3,2-d]pyrimidine, m.p. 112°–113°C (recrystallized from carbon tetrachloride), was prepared from 2-chloro-4-morpholino-pyrido[3,2-d]pyrimidine and dipropanolamine.

EXAMPLE 19

Using a procedure analogous to that described in Example 1, 2-(N-ethanol-hexanolamino)-4-morpholino-pyrido[3,2-d]pyrimidine, m.p. 100°–102°C (recrystallized from ethyl acetate), was prepared from 2-chloro-4-morpholino-pyrido[3,2-d]pyrimidine and N-ethanol-hexanolamine. The yield was 53% of theory.

EXAMPLE 20

Using a procedure analogous to that described in Example 1, (+)-2-piperazino-4-(2'-methyl-morpholino)-pyrido [3,2-d]pyrimidine, m.p. 135°–137°C (recrystallized from cyclohexane), specific rotation $[\alpha]_D^{20} = +43°$ (c = 1.0, methanol), was prepared from (+)-2-chloro-4-(2'-methyl-morpholino)-pyrido[3,2-d]pyrimidine, m.p. 96°–98°C, and piperazine. The yield was 70% of theory. Its dihydrochloride semihydrate had a melting point of 172°C (recrystallized from ethanol) and a specific rotation $[\alpha]_D^{20} = +42°$ (c = 0.91, water).

EXAMPLE 21

Using a procedure analogous to that described in Example 1, (−)-2-piperazino-4-(2'-methyl-morpholino)-pyrido [3,2-d]pyrimidine, m.p. 134°–136°C (recrystallized from cyclohexane), specific rotation $[\alpha]_D^{20} = -43.5°$ (c = 1.0, methanol), was prepared from (−)-2-chloro-4-(2'-methyl-morpholino)-pyrido[3,2-d]pyrimidine, m.p. 99°C, and piperazine. The yield was 73% of theory. Its dihydrochloride semihydrate had a melting point of 170°–172°C (recrystallized from ethanol) and a specific rotation $[\alpha]_D^{20} = -39.5°$ (c = 0.75, water).

EXAMPLE 22

Using a procedure analogous to that described in Example 1, 2-piperazino-4-piperidino-pyrido[3,2-d]pyrimidine, m.p. 113°–114.5°C (recrystallized from cyclohexane), of the formula

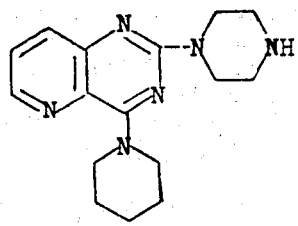

was prepared from 2-chloro-4-piperidino-pyrido[3,2-d]pyrimidine, m.p. 115°–118°C, and piperazine in glycol dimethylether. The yield was 72% of theory.

Using a procedure analogous to that described in Example 1, 2-(dipropanol-amino)-4-piperidino-pyrido[3,2-d]pyrimidine, m.p. 98°–100°C (recrystallized from ethylacetate/petroleum ether = 2:1), was prepared from 2-chloro-4-piperidino-pyrido[3,2-d]pyrimidine and dipropanolamine. The yield was 66% of theory.

EXAMPLE 24

Using a procedure analogous to that described in Example 1, 2-piperazino-4-(1',1'-dioxido-thiomorpholino)-pyrido[3,2-d]pyrimidine, m.p. 208°–210°C (recrystallized from ethanol), of the formula

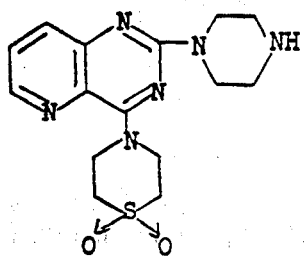

was prepared from 2-chloro-4-(1',1'-dioxido-thiomorpholino)-pyrido[3,2-d]pryimidine, m.p. 256°–258°C, and piperazine. The yield was 75% of theory. Its dihydrochloride had a melting point of 328°–330°C (decomp.; recrystallized from ethanol/water = 8:2).

EXAMPLE 25

Using a procedure analogous to that described in Example 1, 2-thiomorpholino-4-(N'-carbethoxy-piperazino)-pyrido[3,2-d]pyrimidine, m.p. 171.5°–172.5°C (recrystallized from ethyl acetate), of the formula

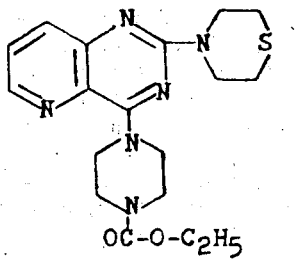

was prepared from 2-chloro-4-(N'-carbethoxy-piperazino)-pyrido[3,2-d]pyrimidine, m.p. 120°–123°C, and thiomorpholine. The yield was 80% of theory.

EXAMPLE 26

Using a procedure analogous to that described in Example 1, 2-(1'-oxido-thiomorpholino)-4-piperazino-pyrido [3,2-d]pyrimidine was prepared from 2-(1'-oxido-thiomorpholino)-4-ethylmercapto-pyrido[3,2-d]pyrimidine (m.p. 199°–200°C) and piperazine at 200°C. Its dihydrochloride had a melting point of 294°–296°C. The yield was 18% of theory.

EXAMPLE 27

2-Thiomorpholino-4-piperazino-pyrido[3,2-d]pyrimidine by method B 9 gm of finely powdered potassium hydroxide were dissolved in 120 ml of boiling isopropanol, the resulting solution was admixed with 12.6 gm of 2-thiomorpholino-4-(N'-carbethoxy-piperazino)-pyrido[3,2-d]pyrimidine, and the mixture was refluxed for eight hours. Thereafter, the reaction solution was evaporated, the residue was admixed with water, and the aqueous mixture was extracted with chloroform. The organic extract solution was washed with water, dried and evaporated, the residue was taken up in hot benzene, the insoluble brown matter was filtered off, and the filtrate was again evaporated. The residue was recrystallized from a small amount of methanol, yielding 6.1 gm (60% of theory) of the compound of the formula

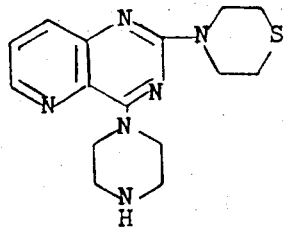

having a melting point of 156°–158°C. Its dihydrochloride, precipitated from ethanol with ethereal hydrochloric acid, had a melting point of 283°–285°C (recrystallized from n-propanol).

EXAMPLE 28

Using a procedure analogous to that described in Example 1, 2-(N'-benzoyl-piperazino)-4-(1'-oxido-thiomorpholino)-pyrido[3,2-d]pyrimidine, m.p. 256°–258°C (recrystallized from ethyl acetate), was prepared from 2-chloro-4-(1'-oxido-thiomorpholino)-pyrido[3,2-d]pyrimidine, m.p. 198°–200°C (decomp.), and N-benzoyl-piperazine.

EXAMPLE 29

Using a procedure analogous to that described in Example 1, 2-(N'-carbethoxy-piperazino)-4-(1'-oxido-thiomorpholino)-pyrido[3,2-d]pyrimidine, m.p. 206°–207°C (recrystallized from ethanol), was prepared from 2-chloro-4-(1'-oxido-thiomorpholino)-pyrido[3,2-d]pyrimidine and N-carbethoxypiperazine.

EXAMPLE 30

Using a procedure analogous to that described in Example 1, 2,4-bis-thiomorpholino-pyrido[3,2-d]pyrimidine, m.p. 134°–135°C (recrystallized from ethanol), of the formula

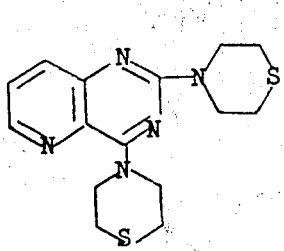

was prepared from 2-chloro-4-thiomorpholino-pyrido[3,2-d]pyrimidine and thiomorpholine. The yield was 49% of theory.

EXAMPLE 31

2,4-Bis-(N'-carbethoxy-piperazino)-pyrido[3,2-d]pyrimidine by method A

A solution of 2.0 gm (10 millimols) of 2,4-dichloropyrido[3,2-d]pyrimidine in 10 ml of dioxane was admixed with 7.1 gm (45 millimols) of N-carbethoxy-piperazine, and the mixture was stirred for 30 minutes at room temperature; however, the 2-chloro-4-(N'-carbethoxy-piperazino)-pyrido[3,2-d]pyrimidine formed thereby was not isolated. The reaction mixture was then refluxed for 4 hours, the resulting reaction solution was evaporated, and the residue was admixed with water, whereby the reaction product slowly crystallized out. The crystals were collected by vacuum filtration, dried and extracted with a large amount of boiling petroleum ether, yielding 2.2 gm (50% of theory) of the compound of the formula

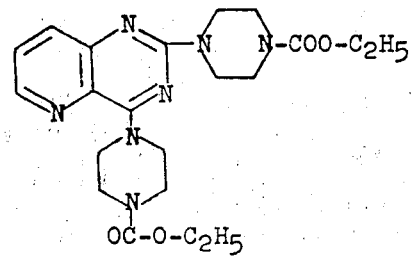

having a melting point of 120°–122°C.

EXAMPLE 32

2-(N'-Acetyl-piperazino)-4-thiomorpholino-pyrido[3,2-d]pyrimidine

A solution of 6.3 gm (20 millimols) of 2-piperazino-4-thiomorpholino-pyrido[3,2-d]pyrimidine in 40 ml of dioxane was admixed with 2.9 ml (30 millimols) of acetic acid anhydride, and then 3.0 gm (30 millimols) of triethylamine were added dropwise to the mixture. The resulting reaction mixture was stirred for three hours at room temperature, then diluted with water, and the precipitate formed thereby was collected and recrystallized from isopropanol, yielding 4.6 gm (65% of theory) of the compound of the formula

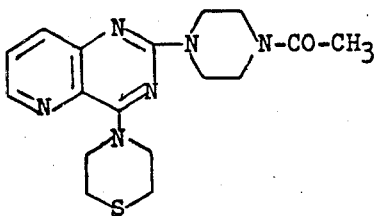

having a melting point of 158°–159°C.

EXAMPLE 33

2-(N'-Methanesulfonyl-piperazino)-4-thiomorpholino-pyrido [3,2-d]pyrimidine, m.p. 218°–219°C (recrystallized from benzene), of the formula

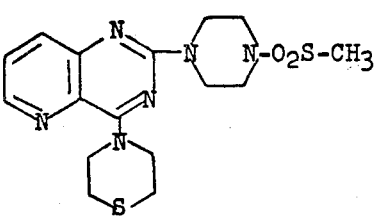

was prepared in a manner analogous to Example 32 from 2-piperazino-4-thiomorpholino-pyrido[3,2-d]pyrimidine and methanesulfonyl chloride in dioxane in the presence of pyridine. The yield was 66% of theory.

EXAMPLE 34

2-(N'-Formyl-piperazino)-4-thiomorpholino-pyrido[3,2-d]pyrimidine

A mixture consisting of 9.5 gm of 2-piperazino-4-thiomorpholino-pyrido[3,2-d]pyrimidine, 7.5 gm of formic acid and 120 ml of toluene was boiled for 90 minutes in a flask provided with a water separator. Thereafter, the toluene was distilled off in vacuo, the residue was admixed with ethyl acetate, and the mixture was refluxed. The insoluble matter was filtered off, the filtrate was admixed with petroleum ether, and the precipitate formed thereby was collected and recrystallized from isopropanol, yielding 7.3 gm (71% of theory) of the compound of the formula

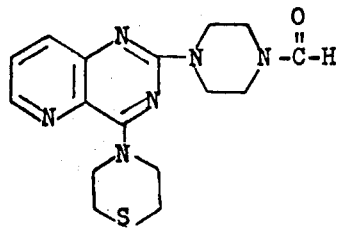

having a melting point of 129.5°–131°C.

EXAMPLE 35

2-(N'-Formyl-piperazino)-4-(1'-oxido-thiomorpholino)-pyrido[3,2-d]pyrimidine

A mixture consisting of 5.6 gm (20 millimols) of 2-chloro-4-(1'-oxido-thiomorpholino)-pyrido[3,2-d]pyrimidine, 4.8 gm (42 millimols) of N-formyl-piperazine and 40 ml of dioxane was refluxed for 4 hours. Thereafter, the solvent was distilled off in vacuo, the residue was admixed with water, the aqueous phase was extracted with methylene chloride, and the organic extract was washed with water, dried, filtered and evaporated in vacuo. The residue was recrystallized from 35 ml of ethyl acetate, yielding 5.6 gm (77.8% of theory) of the above-named product having a melting point of 161°–163°C; upon further recrystallization from isopropanol the product had a melting point of 165°–166°C.

EXAMPLE 36

2-(N'-Aminocarbonyl-piperazino)-4-(1'-oxido-thiomorpholino)-pyrido[3,2-d]pyrimidine A solution of 8.0 gm (20 millimols) of 2-piperazino-4-(1'-oxido-thiomorpholino)-pyrido[3,2-d]pyrimidine dihydrochloride in 40 ml of water was admixed with 1.9 gm (23 millimols) of potassium cyanate, and the resulting mixture was allowed to stand for 15 minutes at room temperature and was then heated for 30 minutes at 40°C. Thereafter, the reaction solution was made alkaline with sodium hydroxide, and the precipitate formed thereby was collected by vacuum filtration, yielding 5.8 gm of the compound of the formula

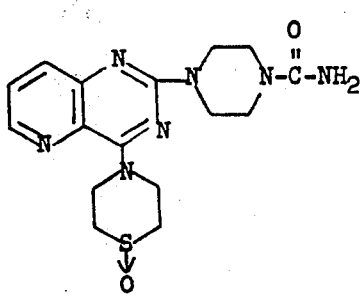

having a melting point of 230°–231°C.

Its hydrochloride, m.p. 190°–192°C (decomp.), prepared by treating the free base with ethanolic hydrochloric acid and recrystallizing the product from ethanol/water (9:1), was obtained with a yield of 6 gm (73% of theory).

EXAMPLE 37

2-Diethanolamino-4-(1'-oxido-thiomorpholino)-pyrido[3,2-d]pyrimidine hydrochloride A mixture consisting of 5.6 gm (20 millimols) of 2-chloro-4-(1'-oxido-thiomorpholino)-pyrido[3,2-d]pyrimidine, 5.2 gm (50 millimols) of diethanolamine and 40 ml of dioxane was refluxed for six hours. Thereafter, the reaction solution was evaporated in vacuo, the residue was admixed with water, the aqueous mixture was extracted with chloroform, and the extract solution was evaporated. The residue was dissolved in ethanol, the resulting solution was acidified with ethanolic hydrochloric acid, and the crystalline precipitate formed thereby was collected, yielding 5.8 gm (75% of theory) of the above-named hydrochloride having a melting point of 232°–233°C.

EXAMPLE 38

2-Piperazino-4-(1'-oxido-thiomorpholino)-6-methyl-pyrido[3,2-]pyrimidine by method A 2.6 gm (9.5 millimols) of 2-chloro-4-(1'-oxido-thiomorpholino)-6-methyl-pyrido[3,2-d]pyrimidine (m.p. 228°–229°C), encased in a liquid-permeable envelope, were extracted therefrom by placing it into a refluxing solution of 3.9 gm (45 millimols) of anhydrous piperazine in 30 ml of dioxane; the extraction was complete after about 2½ hours. Thereafter, the resulting solution was evaporated, the residue was taken up in water, and the precipitate formed thereby was filtered off. The filtrate was extracted ten times with 20 ml each of chloroform/methanol (3:1), and each extract was washed twice with 20 ml of water each. The washed extracts were combined, dried and evaporated, yielding 2.8 gm (68% of theory) of the compound of the formula

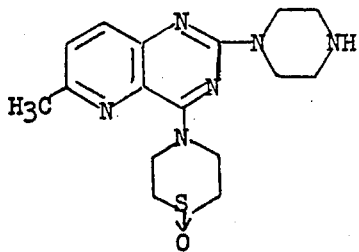

having a melting point of 192°–194°C.

Its dihydrochloride, m.p. 222°–224°C (decomp.), was obtained by adding isopropanolic hydrochloric acid to a solution of the free base in isopropanol.

EXAMPLE 39

2-(N'-Benzoyl-piperazino)-4-(1'-oxido-thiomorpholino)-6-methyl-pyrido[3,2-d]pyrimidine by method A A mixture consisting of 2.96 gm (10 millimols) of 2-chloro-4-(1'-oxido-thiomorpholino)-6-methyl-pyrido[3,2-d]pyrimidine, 5.70 gm (30 millimols) of N-benzoyl-piperazine and 20 ml of dioxane was refluxed for three hours. Thereafter, the reaction solution was diluted with water, and the precipitate formed thereby was collected by vacuum filtration and recrystallized from ethanol, yielding 88% of theory of the compound of the formula

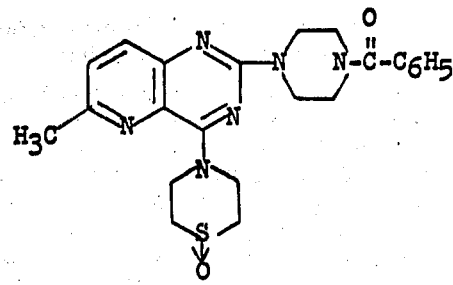

having a melting point of 230°–231°C.

EXAMPLE 40

Using a procedure analogous to that described in Example 38, 2-piperazino-4-thiomorpholino-6-methyl-pyrido[3,2d]pyrimidine was prepared from 2-chloro-4-thiomorpholino-6-methyl-pyrido[3,2-d]pyrimidine, m.p. 150°–151°C, and piperazine hexahydrate at 60°–100°C. The yield was 26% of theory. Its hydrochloride hydrate had a melting point of 304°–306°C (decomp.; recrystallized from methanol).

EXAMPLE 41

Using a procedure analogous to that described in Example 39, 2-(N'-carbethoxy-piperazino)-4-thiomorpholino-6-methyl-pyrido[3,2-d]pyrimidine, m.p. 115°–116°C (recrystallized from cyclohexane was prepared from 2-chloro-4-thiomorpholino-6-methyl-pyrido[3,2-d]pyrimidine and N-carbethoxypiperazine in dioxane. The yield was 71% of theory.

EXAMPLE 42

Using a procedure analogous to that described in Example 38, 2-piperazino-4-(1',1'-dioxido-thiomorpholino)-6-methyl-pyrido[3,2-d]pyrimidine, m.p. 190°–192°C (recrystallized from water), was prepared from 2-chloro-4-(1',1'-dioxide-thiomorpholino)-6-methyl-pyrido[3,2-d]pyrimidine, m.p. 268°–288°C, and piperazine in glycol dimethylether. The yield was 75% of theory. Its dihydrochloride had a melting point of 235°C [decomp.; recrystallized from ethanol/water (85:15)].

EXAMPLE 43

Using a procedure analogous to that described in Example 39, 2-thiomorpholino-4-(N'-carbethoxy-piperazino)-6-methyl-pyrido[3,2-d]pyrimidine, m.p. 157°–158°C (recrystallized from ethyl acetate), was prepared from 2-chloro-4-(N'-carbethoxy-piperazino)-6-methyl-pyrido[3,2-d]pyrimidine, m.p. 172°–173°C, and thiomorpholine in boiling dioxane. The yield was 90% of theory.

EXAMPLE 44

Using a procedure analogous to that described in Example 38, 2-piperazino-4-morpholino-6-methyl-pyrido[3,2-d]pyrimidine was prepared from 2-chloro-4-morpholino-6-methylpyrido[3,2-d]pyrimidine, m.p. 146°–149°C, and piperazine in boiling dioxane. The yield was 65.5% of theory. Its dihydrochloride had a melting point of 320°–322°C (decomp.; recrystallized from ethanol).

EXAMPLE 45

Using a procedure analogous to that described in Example 39, 2-(N'-methyl-piperazino)-4-morpholino-6-methylpyrido[3,2-d]pyrimidine, m.p. 128°–130°C (recrystallized from petroleum ether), was prepared from 2-chloro-4-morpholino-6-methyl-pyrido[3,2-d]pyrimidine, m.p. 146°–149°C, and excess N-methyl-piperazine at 100°C. The yield was 66% of theory. Its dihydrochloride had a melting point of 202°–204°C (decomp.; recrystallized from isopropanol).

EXAMPLE 46

2,4-Bis-thiomorpholino-6-methyl-pyrido[3,2-d]pyrimidine by method A

A solution of 1 gm (3.6 millimols) of 2,4-dichloro-6-methyl-pyrido[3,2-d]pyrimidine (m.p. 152°–154°C; literature m.p. 138°C) in 10 ml of dioxane was admixed with 1.8 gm (18 millimols) of thiomorpholine, and the mixture was allowed to stand overnight at room temperature and was then refluxed for five minutes. Thereafter, the reaction solution was diluted with water, the aqueous mixture was extracted with ethyl acetate, the extract solution was evaporated, and the residue was recrystallized once from petroleum ether and then once from ethanol, yielding 600 mgm (50% of theory) of the compound of the formula

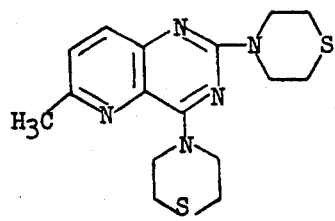

having a melting point of 112°–114°C.

EXAMPLE 47

2-Thiomorpholino-4-piperazino-6-methyl-pyrido[3,2-d]pyrimidine dihydrochloride by method B A mixture consisting of 6.0 gm of 2-thiomorpholino-4-(N'-carbethoxy-piperazine)-6-methyl-pyrido[3,2-d]pyrimidine, 6 gm of potassium hydroxide and 20 ml of isopropanol was refluxed for 20 hours. Thereafter, the reaction solution was evaporated, and the residue was taken up in a mixture of chloroform and water. The organic phase was separated and evaporated, the residue was dissolved in ethanol, the solution was acidified with isopropanolic hydrochloric acid, and the precipitate formed thereby was collected and recrystallized from isopropanol/ethanol (1:1), yielding 27% of theory of the compound of the formula

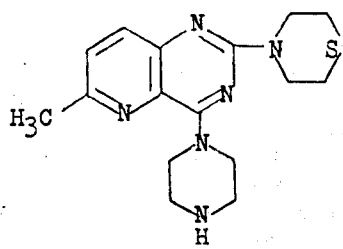

having a melting point of 295°–297°C (decomp.)

The compounds embraced by formula I and their nontoxic, pharmacologically acceptable acid addition salts, have useful pharmacodynamic properties. More particularly, they exhibit a very strong inhibiting action upon thrombocyte aggregation and adhesiveness (platelet stickiness), as well as hypotensive activities, in warm-blooded animals, such as mice, cats and dogs. For instance, the hypotensive activity is particularly pronounced in 4-piperazino-2-(1'-oxido-thiomorpholino)-pyrido[3,2-d]pyrimidine, 4-piperazino-2-thiomorpholino-pyrido[3,2]pyrimidine and 2-piperazino-4-(1'-oxido-thiomorpholino)-pyrido[3,2-d]pyrimidine.

The inhibiting action upon thrombocyte aggregation was ascertained by the method of Born and Cross, J. Physiol. 170, 397 (1964), or by the method of K. Breddin, Schweiz. Med. Wochenschr. 95, 655–660 (1965).

The inhibiting effect upon the platelet stickiness was determined by means of the so-called retention test according to Morris [see E. Deutsch et al, 1.Internationales Symposium uber Stoffwechsel and Membranpermeabilitat von Erythrocyten and Thrombocyten, Vienna, Austria (1969); Georg Thieme Verlag, Stuttgart, Germany].

The prolonging effect upon the bleeding time was ascertained by the method of Duke, J. Amer. Med. Assoc. 15, 1185 (1910).

The hypotensive tests were performed on anesthetized cats and dogs by the method of Eckenhoff, Amer. J. Physiol. 148, 582 (1947).

The table below shows the results obtained from the tests for thrombocyte aggregation inhibition according to the method of Morris and from the tests for prolongation of the bleeding time for a number of representative compounds of the formula I, namely:

A = 2-piperazino-4-thiomorpholinopyrido[3,2-d]pyrimidine maleate,
B = 2-(N'-methyl-piperazino)-4-thiomorpholino-pyrido[3,2-d]pyrimidine dihydrochloride,
C = 2-piperazino-4-(1'-oxido-thiomorpholino)-pyrido[3,2-d]pyrimidine dihydrochloride,
D = 2-(N'-methyl-piperazino)-4-(1'-oxido-thiomorpholino)-pyrido[3,2-d]pyrimidine dihydrochloride,
E = 2-(dipropanol-amino)-4-(1'-oxido-thiomorpholino)-pyrido[3,2-d]pyrimidine hydrochloride,
F = 2-(N-ethanol-hexanolamino)-4-(1'-oxido-thiomorpholino)-pyrido[3,2-d]pyrimidine hydrochloride,
G = 2-piperazino-4-(1'-oxido-2'-methyl-thiomorpholino)-pyrido[3,2-d]pyrimidine dihydrochloride,
H = 2-piperazino-4-morpholino-pyrido[3,2-d]pyrimidine dihydrochloride,
I = 2-(N'-methyl-piperazino)-4-morpholino-pyrido[3,2-d]pyrimidine dihydrochloride,
J = 2-(dipropanol-amino)-4-morpholino-pyrido[3,2-d]pyrimidine dihydrochloride,
K = 2-piperazino-4-piperidino-pyrido[3,2-d]pyrimidine dihydrochloride,
L = 2-(dipropanol-amino)-4-piperidino-pyrido[3,2-d]pyrimidine hydrochloride,
M = 2-piperazino-4-(1',1'-dioxide-thiomorpholino)-pyrido[3,2-d]pyrimidine dihydrochloride,
N = 2-thiomorpholino-4-piperidino-pyrido[3,2-d]pyrimidine dihydrochloride, O = 2-(1'-oxido-thiomorpholino)-4-piperazino-pyride[-methylpyrido[-d]-d]dihydrochloride,
P = 2-piperazino-4-(1'-oxido-thiomorpholino)-6-methylpyrido[3,2-d]pyrimidine dihydrochloride and
Q = 2-thiomorpholino-4-piperazino-6-methyl-pyrido[3,2-d] pyrimidine dihydrochloride.

1. To determine the inhibiting action of the test compound upon thrombocyte aggregation, 1 ml of human blood is pipetted into small test tubes, and the test compound is added to a final concentration of $5\times10^{-5}$ mol/liter. The tubes are incubated for 10 minutes at 37°C. 1 gm of glass beads (glass beads for gas-chromatography) is added to half of the tubes. Finally the closed tubes are attached to a vertical wheel and rotated for 1 minute. By this means good contact is obtained between the glass beads and the blood. The tubes are then allowed to stand at room temperature for another hour, after which time a satisfactory sedimentation of erythrocytes has taken place. 0.01 ml of the supernatant plasma is removed, diluted to 1 : 8,000 with celloscope solution, and the platelet count is read in the celloscope. The percent reduction in the stickiness due to the presence of the substance (compared to tubes without glass beads) is measured and the average of 4 – 6 determinations is taken.

2. To determine the bleeding time, 10 mgm/kg of the test compound is given per os to non-anesthetized mice. After one hour, about 0.5 mm is cut off from the tail of each animal. The exuded blood is soaked up with filter paper every 30 seconds. The number of drops of blood so obtained is used as a measure for the bleeding time compared to untreated animals (5 animals/test).

3. The acute toxicity of some of the compounds for orientation (observation time : 14 days) was determined on mice, or the $LD_{50}$ was calculated from the percentage of animals which died after different doses within the observation time [see J. Pharmacol. exper. Therap. 96, 99(1949)].

TABLE

| Compound | Reduction in Stickiness % | Prolongation of Bleeding Time % | $LD_{50}$ mg/kg p.o. |
| --- | --- | --- | --- |
| A | 99 | 171 | 413 |
| B | 53 | 118 | — |
| C | 99 | — | 872 |
| D | 87 | 88 | — |
| E | 88 | 40 | — |
| F | 71 | 35 | — |
| G | 96 | 55 | — |
| H | 96 | 55 | — |
| I | 70 | 40 | — |
| J | 50 | 45 | — |
| K | 39 | 138 | — |
| L | 20 | 103 | — |
| M | 88 | 98 | >250 (0 out of 10 animals died) |
| N | 77 | 98 | >250 (0 out of 10 animals died) |
| O | 98 | 35 | >250 (0 out of 10 animals died) |
| P | 89 | 98 | — |
| Q | 34 | — | — |

For pharmaceutical purposes the compounds of the formula I or their non-toxic acid addition salts are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds is from 0.083 to 1.67 mgm/kg body weight, preferably 0.16 to 0.84 mgm/kg body weight. The daily dose rate is from 1.66 to 3.34 mgm/kg body weight.

The following examples illustrate a few pharmaceutical dosage unit compositions comprising a compound of the formula I or a non-toxic acid addition salt thereof as an active incredient and represent the best modes contemplated of putting the invention into practical use. The parts are parts by weight unless otherwise specified.

EXAMPLE 48

Tablets

The tablet composition is compounded from the following ingredients:

| | | |
| --- | --- | --- |
| 2-Piperazino-4-thiomorpholino-pyrido[3,2-d]pyrimidine maleate | 30.0 | parts |
| Lactose | 38.0 | parts |
| Potato starch | 26.0 | parts |
| Polyvinylpyrrolidone | 5.0 | parts |
| Magnesium stearate | 1.0 | parts |
| Total | 100.0 | parts |

Preparation

The pyridopyrimidine salt is intimately admixed with the lactose and the potato starch, the mixture is uniformly moistened with an ethanolic 20% solution of the polyvinylpyrrolidone, the moist mass is forced through a 1.5 mm-mesh screen, and the resulting granulate is dried at 45°C. and again passed through a 1.0 mm-mesh screen. The dry granulate thus obtained is admixed with the magnesium stearate, and the composition is compressed into 100 mgm-tablets in a conventional tablet making machine. Each tablet contains 30 mgm of the pyridopyrimidine salt and is an oral dosage unit composition with effective thrombocyte aggregation and stickiness inhibiting action.

EXAMPLE 49

Coated Pills

The pill core composition is compounded from the following ingredients:

| | | |
| --- | --- | --- |
| 2-Piperazino-4-(1'-oxido-thio-morpholino)-pyrido[3,2-d]pyrimidine dihydrochloride | 15.0 | parts |
| Lactose | 14.0 | parts |
| Corn starch | 8.0 | parts |
| Polyvinylpyrrolidone | 2.5 | parts |
| Magnesium stearate | 0.5 | parts |
| Total | 40.0 | parts |

Preparation

The ingredients are compounded in a manner analogous to that described in the preceding example, and the composition is compressed into 40 mgm-pill cores, which are subsequently coated with a thin shell consisting essentially of a mixture of talcum and sugar and finally polished with beeswax. Each coated pill contains 15 mgm of the pyridopyrimidine salt and is an oral dosage unit composition with effective thrombocyte aggregation and stickiness inhibiting action.

EXAMPLE 50

Hypodermic Solution

The solution is compounded from the following ingredients:

| | |
|---|---|
| 2-Piperazino-4-(1'-oxido-2'-methyl-thiomorpholino)-pyrido [3,2-d]pyrimidine dihydrochloride | 10.0 parts |
| Polyethyleneglycol 600 | 100.0 parts |
| Distilled Water q.s.ad | 2000.0 parts by vol. |

Preparation

The polyethyleneglycol and the pyridopyrimidine salt are dissolved in a sufficient amount of distilled water which had previously been boiled and cooled in an atmosphere of nitrogen; the dissolution is also carried out in an atmosphere of nitrogen. The resulting solution is diluted to the indicated volume with additional pretreated distilled water, and the resulting solution is filled, again in an atmosphere of nitrogen, into brown 2 cc-ampules which are then sterilized for 20 minutes at 120°C. and subsequently sealed. The entire operation must be performed in diffused light. Each ampule contains 10 mgm of the pyridopyrimidine salt, and the contents thereof are an injectable dosage unit composition with effective thrombocyte aggregation and stickiness inhibiting action.

EXAMPLE 51

Drop Solution

The solution is compounded from the following ingredients:

| | |
|---|---|
| 2-Piperazino-4-morpholino-pyrido[3,2-d]pyrimidine dihydrochloride | 10.0 parts |
| Cane sugar | 350.0 parts |
| Sorbic acid | 1.0 part |
| Essence of cocoa | 50.0 parts |
| Ethyl alcohol | 200.0 parts by vol. |
| Polyethyleneglycol 600 | 100.0 parts by vol. |
| Distilled water q.s.ad | 1000.0 parts by vol. |

Preparation

The sorbic acid is dissolved in the ethanol, the solution is diluted with an equal volume of distilled water, and the pyridopyrimidine salt is dissolved in the aqueous mixture (solution 1). The cane sugar is dissolved in the remaining amount of distilled water (solution 2). Solution 2, the polyethyleneglycol and the essence of cocoa are stirred into solution 1, and the composition is filtered. The entire operation must be performed in an atmosphere of nitrogen and in diffused light. 1 ml of the filtrate (about 20 drops) contains 10 mgm of the pyridopyrimidine salt and is an oral dosage unit composition with effective thrombocyte aggregation and stickiness inhibiting action.

Analogous results are obtained when any one of the other pyridopyrimidines embraced by formula I or a nontoxic acid addition salt thereof is substituted for the particular pyridopyrimidine in Examples 48 through 51. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An antithrombotic pharmaceutical dosage unit composition consisting essentially of an inert pharmaceutical carrier and an effective antithrombotic amount of a compound of the formula

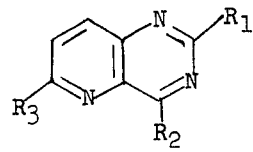

wherein
$R_1$ and $R_2$ are each morpholino, thiomorpholino, 1-oxido-thiomorpholino, 1,1-dioxido-thiomorpholino or piperidino, where each of these may optionally have a methyl substituent attached thereto; piperazino; N'-formyl-piperazino; N'-acetyl-piperazino; N'-carbethoxy-piperazino; N'-benzoyl-piperazino; N'-methanesulfonyl-piperazino; N'-p-toluenesulfonyl-piperazino; N'-carbamoyl-piperazino; N'-methyl-piperazino; di(alkanol of 2 to 6 carbon atoms)-amino; or ethylenediamino; and
$R_3$ is hydrogen or methyl;
or a non-toxic, pharmacologically acceptable acid addition salt thereof.

2. A composition according to claim 1, wherein one of $R_1$ and $R_2$ is unsubstituted piperazino and the other is thiomorpholino, 1-oxido-thiomorpholino or 1,1-dioxido-thiomorpholino, where each of these may optionally be methyl-substituted, and $R_3$ is hydrogen or methyl, or a non-toxic, pharmacologically acceptable acid addition salt thereof.

3. A composition of claim 1, wherein said compound is 2-piperazino-4-thiomorpholino-pyrido [3,2-d] pyrimidine or a non-toxic, pharmacologically acceptable acid addition salt thereof.

4. A composition of claim 1, wherein said compound is 4-piperazino-2-thiomorpholino-pyrido [3,2-d] pyrimidine or a non-toxic, pharmacologically acceptable acid addition salt thereof.

5. A composition of claim 1, wherein said compound is 2-piperazino-4-(1'-Oxido-thiomorpholino)-pyrido [3,2-d] pyrimidine or a non-toxic, pharmacologically acceptable acid addition salt thereof.

6. A composition of claim 1, wherein said compound is 4-piperazino-2-(1'-oxido-thiomorpholino)-pyrido [3,2-d] pyrimidine or a non-toxic, pharmacologically acceptable acid addition salt thereof.

7. A composition of claim 1, wherein said compound is 2-piperazino-4-(1'-oxido-thiomorpholino)-6-methyl-pyrido [3,2-d]-pyrimidine or a non-toxic, pharmacologically acceptable acid salt thereof.

8. A composition of claim 1, wherein said compound is 2-thiomorpholino-4-piperazino-6-methyl-pyrido [3,2-d] pyrimidine or a non-toxic, pharmacologocally acceptable acid salt thereof.

9. The method of inhibiting thrombocyte aggregation and adhesiveness in a warm-blooded animal in need of such treatment, which comprises perorally or parenterally administering to said animal a composition of claim 1.

* * * * *

UNITED STATES PATENT OFFICE
CERTIFICATE OF CORRECTION

Patent No. 3,939,268    Dated February 17, 1976

Inventor(s) JOSEF NICKL; ERICH MULLER; BERTHOLD NARR; JOSEF ROCH

It is certified that error appears in the above-identified patent and that said Letters Patent are hereby corrected as shown below:

| | |
|---|---|
| In Col. 2, Line 55 | "hydrochloride" should read -- hydrochloric -- |
| In Col. 4, Line 51 | "72of" should read -- 72% of -- |
| In Col. 10, Between lines 44 and 45 | -- Example 23 -- has been omitted |
| In Col. 19, Line 2 | "pyride [-methylpyrido[-d]-d]" should read -- pyrido [3,2-d] pyrimidine -- |

Signed and Sealed this eighteenth Day of May 1976

[SEAL]

Attest:

RUTH C. MASON
Attesting Officer

C. MARSHALL DANN
Commissioner of Patents and Trademarks